(12) United States Patent
Rebec

(10) Patent No.: US 8,032,197 B2
(45) Date of Patent: Oct. 4, 2011

(54) METHOD OF ANALYZING FOR AT LEAST ONE DISEASE OR CONDITION MARKER

(75) Inventor: Mihailo V. Rebec, Bristol, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 289 days.

(21) Appl. No.: 11/999,634

(22) Filed: Dec. 6, 2007

(65) Prior Publication Data

US 2008/0154106 A1   Jun. 26, 2008

Related U.S. Application Data

(60) Provisional application No. 60/876,300, filed on Dec. 21, 2006.

(51) Int. Cl.
*A61B 5/05* (2006.01)

(52) U.S. Cl. ......... 600/345; 600/347; 600/365; 600/309

(58) Field of Classification Search .......... 600/345, 600/347, 309, 310, 316, 317, 322, 341, 354, 600/362, 365, 483

See application file for complete search history.

(56) References Cited

U.S. PATENT DOCUMENTS

| 6,272,364 | B1 * | 8/2001 | Kurnik ............... 600/345 |
| 2004/0133086 | A1 * | 7/2004 | Ciurczak et al. ....... 600/322 |
| 2005/0182307 | A1 * | 8/2005 | Currie et al. .......... 600/300 |
| 2006/0015058 | A1 * | 1/2006 | Kellogg et al. ........ 604/22 |

\* cited by examiner

*Primary Examiner* — Charles A Marmor, II
*Assistant Examiner* — Michael D'Angelo
(74) *Attorney, Agent, or Firm* — Nixon Peabody LLP

(57) ABSTRACT

A method of using a diffusion-based, continuous-monitoring system to analyze for a disease or condition includes creating a diffusion channel in an area of skin. The diffusion channel is maintained for a desired duration. The level of the disease marker(s) is continuously monitored for the desired duration via a diffusion-based, continuous-monitoring device. The levels of the at least one disease marker at the area of skin are analyzed to determine if the disease or condition associated with the at least one disease marker is present.

17 Claims, 1 Drawing Sheet

METHOD OF ANALYZING FOR AT LEAST ONE DISEASE OR CONDITION MARKER

CROSS REFERENCE TO RELATED APPLICATION

This application claims priority to application Ser. No. 60/876,300 filed on Dec. 21, 2006, which is incorporated by reference in its entirety.

FIELD OF THE INVENTION

The present invention relates generally to a method of analyzing for at least one disease marker and, more specifically, to a method of diffusion-based, continuous disease marker analyzation.

BACKGROUND OF THE INVENTION

There are many diseases or conditions that can be harmful or even fatal to individuals. Some of these diseases can be monitored by the use of markers. For example, heart attacks can be monitored by enzymes such as troponin (TnI, TnT), creatine phosphokinase (CPK, CK), lactate dehydrogenase (LD), and aspartate transaminase (AST) in the blood. Low levels of these enzymes are normally found in your blood, but if your heart muscle is injured, such as from a heart attack, enzymes leak out of damaged heart muscle cells and their levels in the bloodstream rise. It would be desirable to have a method of monitoring for markers such as selected enzymes for heart attacks and other diseases or conditions.

SUMMARY OF THE INVENTION

According to one method, a diffusion-based, continuous-monitoring system is used to analyze for a state of a disease or condition. At least one diffusion channel is created in an area of skin. The at least one diffusion channel is maintained for a desired duration. The level of at least one disease marker is continuously monitored for the desired duration via a diffusion-based, continuous-monitoring device. The levels of the at least one disease marker at the area of skin are analyzed to determine if the disease or condition associated with the at least one disease or condition marker is present.

According to another method, a diffusion-based, continuous-monitoring system is used to analyze for a state of at least one disease or condition. A diffusion-based, continuous-monitoring device is provided. The device includes a communications interface that is adapted to connect with a receiving module via a communications link. At least one diffusion channel is created in an area of skin. The at least one diffusion channel is maintained for a desired duration. The level of at least one disease marker for the desired duration is continuously monitored via the diffusion-based, continuous-monitoring device. The levels of the at least one disease marker at the area of skin are analyzed to determine if the disease or condition associated with the at least one disease marker is present.

According to a further method, a diffusion-based, continuous-monitoring system is used to analyze for a heart attack. At least one diffusion channel is created in an area of skin. The at least one diffusion channel is maintained for a desired duration. The level of at least one of troponin, creatine phosphokinase, lactate dehydrogenase, and aspartate transaminase is continuously monitored via a diffusion-based, continuous monitoring device. The levels of the at least one of troponin, creatine phosphokinase, lactate dehydrogenase, and aspartate transaminase at the area of skin is analyzed to determine the presence of a heart attack.

According to a yet another method, a diffusion-based, continuous-monitoring system to analyze for kidney disease is used. At least one diffusion channel is created in an area of skin. The at least one diffusion channel is maintained for a desired duration. The level of blood urea nitrogen and/or creatinine is continuously monitored via a diffusion-based, continuous monitoring device. The levels of the blood urea nitrogen and/or creatinine at the area of skin are analyzed to determine if kidney disease is present.

Figure 1:
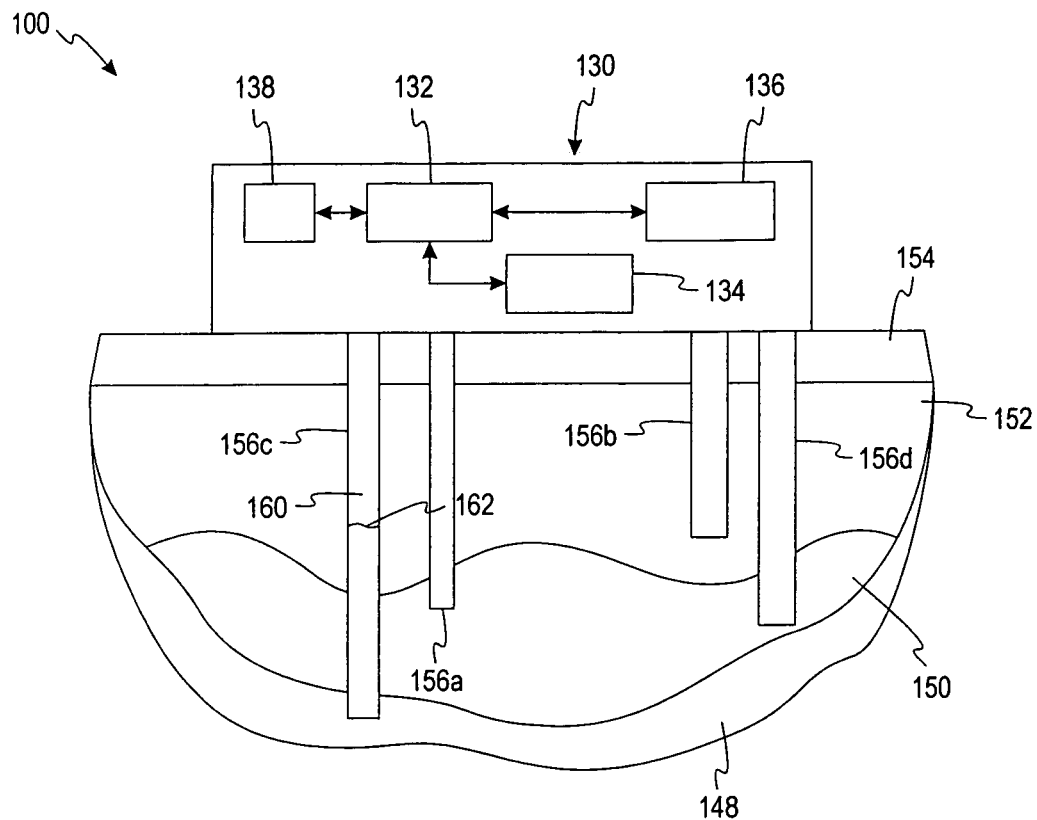
FIG. 1 is a diffusion-based, continuous-monitoring system shown in a transdermal application according to one embodiment.

While the invention is susceptible to various modifications and alternative forms, specific embodiments are shown by way of example in the drawings and are described in detail herein. It should be understood, however, that the invention is not intended to be limited to the particular forms disclosed.

DETAILED DESCRIPTION OF THE ILLUSTRATED EMBODIMENTS

The present invention is directed to a method of using a diffusion-based, continuous-monitoring system to analyze for at least one disease or condition marker in an area of the skin. By continuously monitoring the level of a disease or condition marker at an area of skin, it can be determined whether there is an alleviated risk or the actual occurrence of a condition or disease. Additionally, by continuously monitoring the level of a disease or condition, the severity and progression of the disease or condition can be determined. The disease or condition marker may be analyzed in, for example, body fluids like ISF (interstitial fluid), whole blood sample, intracellular and intercellular fluids.

The term "level" is defined herein as including any information related to the amount, relative concentration, absolute concentration and ratios of the disease or condition marker to assist in analyzing for a disease or condition. The term "level" as defined herein also includes changes in the amount, relative and absolute concentrations, and ratios whether in a percentage or absolute context. These "level" changes may be used over a selected duration of time such as, for example, a time change in amount, concentration or ratio. The "level" may refer to a time change in amount, concentration or ratio and compared to a later time change. The amount and rate of change of these disease/condition markers are powerful tools in assessing the physiological state of the individual.

The disease or condition marker may vary depending on the disease or condition that is being continuously monitored. For example, heart attacks may be monitored by enzymes such as troponin (TnI, TnT), creatine phosphokinase (CPK, CK), lactate dehydrogenase (LD), and aspartate transaminase (AST) in the blood. Low levels of these enzymes are normally found in your blood, but if your heart muscle is injured, such as from a heart attack, enzymes leak out of damaged heart muscle cells and their levels in the bloodstream rise. The production of such enzymes, ratios of these enzymes and/or the ratios of their isoenzymes to each other in a body fluid may be identified and quantified. Such information about the presence of such enzymes, ratios of these enzymes and/or ratios of their isoenzymes may provide valuable information on the state or progression of the disease or condition and the time duration after a myocardial infract. Additionally, information about the time of the heart attack as well as subsequent attacks that may be occurring can also be determined.

It is contemplated that other diseases or conditions may be continuously monitored such as kidney disease, liver disease, viral diseases (e.g., viral hepatitis) chemotherapy, radiation therapy, and long-term chronic diseases such as arthritis. It is contemplated that other conditions/diseases may be monitored.

Kidney disease may involve the kidneys not working at all or the kidneys not working at full capacity. For example, blood urea nitrogen (BUN) and/or creatinine may be continuously monitored to determine how efficient the kidneys are operating. Healthy kidneys take urea out of the blood and put it into urine. If the kidneys are not working well, the blood urea nitrogen (BUN) will stay in the blood. A normal range for BUN is generally from about 15 to about 30 mg/dl with elevated values being greater than about 35 or 50 mg/dl. The BUN number can be in excess of 80 mg/dl. If the BUN number is elevated (e.g., above about 35 or 50 mg/dL), the kidneys may not be working at full strength.

Similarly, healthy kidneys take creatinine from the blood and put it into urine to leave the body. Thus, creatinine is a product-extraction component. When kidneys are not working well, creatinine builds up in the blood. Creatinine values can vary and may be affected by diet, but are generally from about 0.6 to about 1.2 mg/dL in individuals. If the creatinine level is greater than about 1.7 mg/dL for most men and greater than 1.4 mg/dL for most women, then there may be a problem with the kidneys. If the creatinine levels are over about 8 mg/dL, this is an indication of hemolytic uremic syndrome. These creatinine levels would be tracked closely when dealing with kidney failure and the need for dialysis treatment. Thus, tracking the creatinine levels assists in determining the effectiveness of the dialysis treatment. Thus, the progression of kidney disease can be monitored.

According to one method, at least three criteria may be considered in selecting a suitable diffusion-based, continuous-monitoring system to analyze disease or condition markers in a body fluid sample from an area of skin. First, a diffusion-enhancing process for the skin is selected. Second, a material is selected to assist in maintaining contact with the skin and further enhance diffusion of the disease or condition markers in the body fluid sample from an area of skin. Third, a diffusion-based, continuous-monitoring system is selected to monitor the disease or condition markers in the body fluid sample that are diffused from the skin.

According to one method, the diffusion-enhancing process for the skin is selected based on factors such as the following: length of time of testing, the disease or condition markers (e.g., enzymes) to be analyzed, and the area of the skin from where the disease or condition markers are located. As shown above, the disease or condition markers do not have to be enzymes, but rather are indicators of the disease or condition state. The disease or condition markers indicate that there has been damage to some tissue and the damage results in the release of intercellular materials such as enzymes, BUN, creatinine, potassium, sodium and chloride. The disease or condition markers are used to determine the extent of damage or changes in cellular functions. It is contemplated that other disease or condition markers may be used. It is desirable for the diffusion-enhancing process to maintain the diffusion channel throughout the desired time period.

Skin abrasion is typically selected when the continuous-testing period is a relatively short period of time (e.g., less than about 8 hours). Skin abrasion is desirable for a shorter continuous-testing period because of the minimum impact on the skin. It is contemplated that a number of skin-abrasion techniques may be used. In one technique, skin abrasion occurs using a gel material including pumas or other skin-abrasion materials. In this technique, the gel material including pumas or other skin-abrasion materials is rubbed on the skin to increase the permeability of the skin. Skin abrasion may occur by other techniques such as using a generally coarse material (e.g., sandpaper), tape peeling or pumas paper.

To increase the porosity of skin (e.g., the stratum cornium, epidermis and/or dermis), chemical agents and physical agents may be used. The chemical and physical agents desirably assist in breaking down the lipids on the stratum cornium. The chemical and physical agents are typically used in short-term solutions and medium-term solutions. It is contemplated, however, that the chemical and physical agents may be used in long-term solutions.

The chemical agents may be skin hydration or skin exfoliates that increase the hydration and porosity of the skin. Skin hydration/exfoliates may include those commercially used in skin products. Some non-limiting examples of chemical agents that may be used include d-limonene, L-limonene, and alpha-terpinene. These chemical agents act by extracting lipids from, for example, the stratum cornium, which result in the disruption of the stratum cornium and desquamated stratum cornium flake.

There are number of physical processes that can be used to enhance the permeability of the skin so as to increase the diffusion of the monitored disease or condition marker of interest. In one process, needle-less jet injectors are used with very fine, particulates of inert material that are fired directly into the skin using high-pressure gas. In another process, pulsed magnetic fields may be used to create transient pores in the skin, resulting in increased permeation. It is contemplated that other physical processes may be used to enhance the permeability of the skin.

If the continuous-testing period is longer (e.g., from about 8 hours to 24 hours), then a different diffusion-enhancing approach may be selected. For such a period, various approaches may be selected such as microporation, microneedle-diffusion enhancement, pressure members, multiple lances, heavier abrasions and ultrasound energy.

In one method, a microporation or a microneedle-diffusion enhancement approach may be used for longer continuous testing periods. A microporation approach creates sub-millimeter size apertures in the epidermis. In one microporation technique, a laser-poration technique may be used to deliver laser power directly to the skin to create apertures or pores. Laser-poration techniques are typically used to form shallow apertures or pores.

In a further method, a series of absorbing dots is located in the stratum cornium and then followed by delivery of a laser that absorbs and softens at each point. The absorbent material converts the laser power to heat, which combined with pressure, create the apertures in the stratum cornium.

A microneedle-diffusion enhancement approach creates apertures in the epidermis and dermis. In another method, a pressure member is adapted to apply pressure to and stretch the skin in preparation for forming a tear in the skin. In another approach, a heavier abrasion of the skin could be performed such as using a more coarse material. An example of a more coarse material includes, but is not limited to, coarser sandpaper.

In another method, ultrasound energy is used to disrupt the lipid bilayer of the stratum cornium so as to increase the skin permeability. Ultrasound energy typically forms shallow apertures. By increasing the skin permeability, the amount of interstitial fluid (ISF) used in monitoring the disease markers is increased. One non-limiting source of an ultrasound energy system is Sontra SonoPrep® ultrasonic skin permeation system marketed by Sontra Medical Corporation. The Sono-Prep® system applies relatively low frequency ultrasonic energy to the skin for a limited duration (from about 10 to 20 seconds). The ultrasonic horn contained in the device vibrates at about 55,000 times per second (55 KHz) and applies energy to the skin through the liquid medium (e.g., hydrogel or liquid) to create cavitation bubbles that expand and contract in the liquid medium.

The chemical and physical agents discussed above in the generally short term can also be used in medium continuous-testing periods to increase and maintain the porosity of the skin. It is contemplated, however, that the chemical and physical agents may be used to obtain longer term action. For example, delipidating agents may be used in combination with physical agents such as ultrasonic preparation to create more long term diffusional channels.

If the continuous-testing period is even longer (e.g., at least 24 hours to about 48 hours), a deep, laser-ablation technique or lance may be selected. A deep, laser-ablation technique is desirable because the monitoring process can function longer due to the time needed to close the aperture created in the skin. The laser-ablation technique typically forms wide apertures. It is contemplated that a microneedle diffusion-enhancing approach, laser poration or lancets may also be used to provide a deeper aperture.

The size of the disease or condition marker to be analyzed may also affect the diffusion-enhancing technique to be used. If the disease or condition markers are large molecules, the diffusion-enhancing process would desirably form a larger aperture in the skin. Similarly, if smaller disease or condition markers are to be monitored, the diffusion-enhancing process desirably would form a smaller aperture in the skin.

The area of the skin where the disease or condition marker is located is also a consideration in selecting the diffusion-enhancing process. For example, if the epidermis or the upper part of the dermis is where the disease or condition marker is to be monitored, the diffusion-enhancing process would be selected to disrupt the stratum cornium. Examples of such diffusion-enhancing processes include skin abrasion, skin hydrations (which increase the hydration of the skin) and skin exfoliates.

If monitoring of the disease or condition markers in the ISF of the lower dermis is desired, the diffusion-enhancing process is selected to create diffusion channels deep into the dermis. If monitoring of the disease or condition markers in the ISF or the subcutaneous region is desired, the diffusion-enhancing process is selected to create diffusion channels through the dermis into the subcutaneous region. Non-limiting examples of diffusion-enhancing processes that create deep diffusion channels into the dermis or subcutaneous region include, but are not limited to, laser poration, microneedles and lancets. It is also contemplated that an electric discharge with high energy and conductivity may also be used to create deep diffusion channels.

The chemical and physical agents discussed above in the generally short term may also be used in longer continuous-testing periods to increase and maintain the porosity of the skin.

In addition to selecting a continuous diffusion-enhancing method, a material is selected to assist in maintaining contact with the skin and to match the monitoring requirements in one method. The diffusion-enhancing material maintains desirable skin contact at all times and assists in maintaining the diffusion channel. The material may be selected based on factors such as the following: length of monitoring time, the disease or condition markers to be monitored, and the area of the skin from where the disease or condition markers are located. For example, the viscosity of the material may be matched with the disease or condition markers to be monitored. More specifically, the viscosity would be the choice of material based on the size of the desired analyte. For example, if changes in the potassium level are being monitored, a small porosity, high viscosity material is typically desirable since the diffusion rates of potassium are relatively fast. In another example, if changes in a relatively large molecular item (e.g., protein) are being monitored, then a low viscosity material would be typically selected.

Examples of diffusion-enhancing materials that may be used in the diffusion-based, continuous-monitoring system include, but are not limited to, hydrogels, liquids and a liquid-stabilizing layer containing a liquid or hydrogel. The diffusion-enhancing material also desirably assists in hydrating the skin and maintaining an opening in the skin. By maintaining the opening, a liquid bridge is formed such that the disease or condition markers diffuse from a layer in the skin through the opening. The liquid bridge may be between a hydrogel/liquid and a body fluid such as ISF (interstitial fluid) or a whole blood sample.

The hydrogels typically have high water content and tacky characteristics. Hydrogels assist in carrying the disease or condition marker to the skin surface and hydrating the skin. Hydrogels are typically used with smaller sized disease or condition marker molecules, shorter analysis times and an upper dermis analysis site.

A hydrogel composition is defined herein as including a cross-linked polymer gel. The hydrogel composition generally comprises at least one monomer and a solvent. The solvent is typically substantially biocompatible with the skin. Non-limiting examples of solvents that may be used in the hydrogel composition include water and a water mixture. The amount of solvent in the hydrogel is generally from about 10 to about 95 weight percent and may vary depending on the monomer amount, crosslinking, and/or the desired composition of the gel. One non-limiting example of a hydrogel/liquid is dimethylsulfoxide (DMSO). DMSO also assists in solubilizing lipids. An example of a liquid that may be used include alcohol in combination with water. It is contemplated that other hydrogels/liquids may be used.

The hydrogel/liquid may be located in a material (i.e., a liquid-stabilizing layer). This material may be selected to assist in maintaining contact with the skin as well as being able to retain the hydrogel/liquid. The liquid-stabilizing layer may include a chamber where the disease or condition markers of interest can diffuse. One non-limiting example of a material that can be used is a sponge or spongy material. The spongy material includes unbound liquid such as water and provides some structure to the unbound water. The spongy material is typically used with larger sized disease or condition markers, longer monitoring time and deeper monitoring sites.

The amount of hydrogel that is selected is based on the need to provide a hydrated skin and having the hydrogel remain in intimate contact with the skin. One disadvantage of using a large amount of hydrogel is the potential impact on the lag time of the disease or condition marker diffusing to the diffusion-based, continuous-monitoring system and/or the analysis components reaching the skin. Such occurrences may potentially impact the analysis time.

Other materials may be used to create content with skin and conduct further analysis. Materials include, but are not limited to, woven materials, non-woven materials, and polymeric films with apertures or porations formed therein. The polymeric films may, for example, be cast polymeric films. These materials may be used with liquids to facilitate diffusion of the disease markers from the skin.

Additives may be added to the hydrogel or liquid. For example, to assist in dissolving lipids, the hydrogel or liquid may include SDS (sodium dodecyl (lauryl) sulfate) or SLS (sodium lauryl (laureth) sulfate). It is contemplated that other additives may be included in the hydrogel or liquid to assist in dissolving the lipids such as soaps. In another embodiment, DMSO may be used as an additive to another hydrogel/liquid to assist in solubilizing lipids. Additional analysis components may also be added to the hydrogels/liquids.

In another embodiment, an interference-filtering component may be added to the hydrogels/liquids. These interference-filtering components may include size exclusion, interference-binding molecules, and/or molecules that remove or convert interfering substances. Some non-limiting examples of interference-binding molecules are antibodies or materials with appropriate charges. Another example is changing the ionic charge nature of the hydrogel or diffusion matrix such that charged interference molecules are inhibited from getting to the surface of the sensor.

Hypertonic solutions, hypotonic solutions and buffered solutions may be used as a diffusion-enhancing material. Hypertonic solutions are solutions having a high solute concentration, while hypotonic solutions are solutions having a low solute concentration. Hypertonic solutions assist in driving up the body fluid (e.g., ISF) closer to the skin surface. Hypotonic solutions, on the other hand, assist in driving up the disease or condition markers closer to the skin surface. The hypertonic or hypotonic solutions in one embodiment may be included with the hydrogel or liquid.

To assist in analyzing the disease or condition markers of interest, a charged additive may be added to the hydrogel or liquid. In one embodiment, a cationic surfactant is added to the hydrogel or liquid. In another example, an anionic surfactant is added to the hydrogel or liquid.

It is contemplated that other additives may be added to the hydrogel or the liquids to assist in monitoring the disease or condition markers.

A diffusion-based, continuous-monitoring device is selected that monitors the disease or condition marker of the body fluid sample that is diffused from the skin. The diffusion-based, continuous-monitoring device may be selected from an electrochemical-monitoring system, an optical-monitoring system, an osmotic-monitoring system and a pressure-based monitoring system. A pressure-based monitoring system includes systems associated with the binding of a disease or condition marker by components of the hydrogel, which results in a volume change in the gel. The monitoring may be performed in a vertical or horizontal direction with respect to the diffusion channel(s) formed in the skin. It is contemplated that the disease or condition marker may be carried out in the material that is selected to assist in maintaining contact with the skin (e.g., the hydrogel or liquid).

The diffusion-based, continuous-monitoring device is typically located near or at the skin. The diffusion-based, continuous-monitoring device may be coupled with the skin and is typically in intimate contact with the skin. For example, the diffusion-based, continuous-monitoring device may be adhered to the skin with an adhesive. The adhesive may be the hydrogel itself. In another embodiment, the adhesive is a separate component whose sole function is to adhere the continuous-monitoring device to the skin. In a further method, the diffusion-based, continuous-monitoring device may be coupled to the skin by a mechanical attachment. For example, the mechanical attachment may be a wrist band (e.g., an elastic band, a watch band, a band with an attachment mechanism such as a hook and loop mechanism). One example of a hook and loop mechanism is a Velcro® strap marketed by 3M Corporation of St. Paul, Minn. It is contemplated that other mechanical attachments may be used to couple or attach the continuous-monitoring device with skin.

The diffusion-based, continuous-monitoring device may have a variety of forms. For example, the continuous-monitoring device may be a pad, circular disk, polygonal shaped or non-polygonal shaped. The continuous-monitoring system may include the analysis element. For example, a pad with an analysis element may be used instead of, or in addition to, the analysis element being initially located in the hydrogel or liquid. In one embodiment, the analysis component may be initially located in the continuous-monitoring device.

In one embodiment, the diffusion-based, continuous-monitoring device includes a processor to process the data, a memory that stores data, and a communications interface. The data may be stored at regular intervals such as, for example, every minute, every 5 minutes or every 30 minutes. The intervals may be shorter such as every second or longer such as being several hours apart. For example, cardiac enzyme assessments may have intervals of up to three or four hours apart. The selected intervals depends on the marker being tracked and the rate of change of that marker. It is contemplated that other regular or non-regular intervals may be used to store the data.

The data may be any information that assists in monitoring the disease markers. This may include the level of disease or condition markers, the ratios of disease or condition markers, the amount of damage, and time progressions of the disease or condition markers. This information may then be processed to determine a course of action to address the disease or condition. By storing the data in the continuous-monitoring device, this data can be accessed and used to assist in monitoring the disease or condition. It is desirable for the continuous-monitoring device to tabulate, transmit and store information that assists in monitoring the disease or condition.

In one embodiment, the continuous-monitoring device is connected to a remote-monitoring system over a communications link. The communications link between the continuous-monitoring device and the remote-monitoring system may be wireless, hard wired or a combination thereof. The wireless communications link may include an RF link, an infrared link or an inductive magnetic link. The wireless implementation may include an internet connection. The continuous-monitoring device may communicate via its communication interface with devices such as a computer, e-mail server, cell phone or telephone. It is contemplated that the continuous-monitoring device may include other devices that are capable of storing, sending and/or receiving information.

The remote-monitoring system enables an individual such as a physician to monitor the disease or condition markers from a remote location. The remote-monitoring system may be located in, for example, a hospital. The physician may be able to access information from the continuous-monitoring device via its communications interface using, for example, a computer or telephone. The remote-monitoring system is especially desirable for patients who are less lucid and need assistance with monitoring selected disease or condition markers. It is desirable for the remote-monitoring system to be able to display, calibrate and store information received from the continuous-monitoring device.

In one method, the continuous-monitoring device may forward information over a communications link in real-time. In another method, the continuous-monitoring device may store and process the data before forwarding the information over a communications link in another embodiment.

Figure 2:
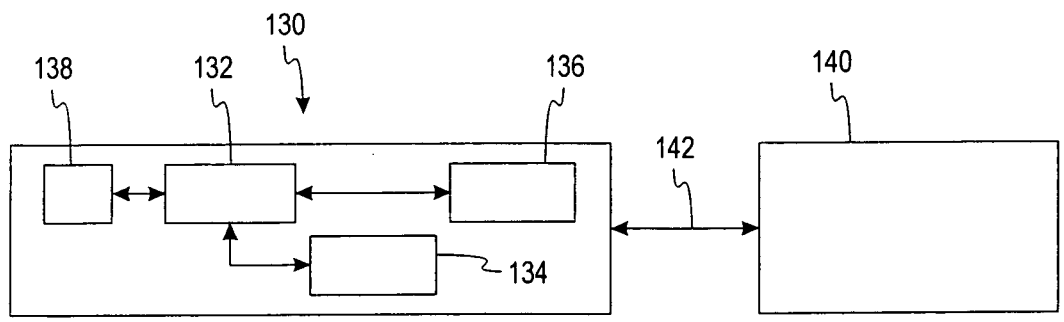
FIG. 2 is the continuous-monitoring system of FIG. 1 being connected to a receiving module.

Referring to FIG. 1, a diffusion-based, continuous-monitoring system 100 is shown in a transdermal application. The continuous-monitoring system 100 includes a continuous-monitoring device 130 being placed above skin. The continuous-monitoring device 130 of FIG. 1 includes a processor 132, memory 134, a communication interface 136 and an analysis component 138. Referring to FIG. 2, the continuous-monitoring device 130 is shown in communication with a receiving module 140 (e.g., a remote-monitoring station) over a communications link 142.

The skin as shown in FIG. 1 includes a subcutaneous layer 148, a dermis layer 150, an epidermis layer 152 and a stratum corneum layer 154. The stratum corneum layer 154 has a plurality of channels 156a-d formed therein. The plurality of channels 156a-d may be formed by different methods such as discussed above. The channels may be of different sizes and depths depending on the disease or condition markers being analyzed and the location of the disease or condition markers in the skin. The disease or condition markers of interest may be located in the different layers of the skin. The disease or condition markers of interest are primarily located in the dermis layer 150 or the subcutaneous layer 148. The hydrogel/liquid assists in diffusing the disease or condition markers to the surface of the skin. The channel 156c is shown with hydrogel/liquid 160.

In one method, a hydrogel/liquid is used to assist in diffusing the disease/condition marker to the surface of the skin. The channel 156c is shown with hydrogel/liquid 160. An interface 162 is formed between the hydrogel/liquid and the body fluid. The analysis may be performed in several locations in the continuous-monitoring system 100. For example, the analysis may be performed using the analysis components 138 in the continuous-monitoring device 130. The analysis components may include components such as a sensor, an enzyme or reagent, potentiostat, electrochemical analysis components (e.g., plurality of electrodes, etc.) and/or optical analysis components (e.g., light source, detector, etc.). In another example, the analysis may be performed on the skin and/or in the channels. It is contemplated that the analysis may take place in more than one location. For example, the hydrogel/liquid may include an analysis portion (e.g., a reagent or enzyme) that reacts with disease/condition marker in the channel, while the remainder of the analysis takes place on the skin or in the continuous-monitoring device 130.

According to one process, a technician programs the diffusion-based, continuous-monitoring device for operation. The technician may program, for example, the disease or condition markers to be monitored, the length of time of the monitoring and ratios of disease or condition markers to be monitored. The technician may then proceed to form apertures in the skin to form the desired diffusion channels as discussed above for the desired time period. The technician locates the continuous-monitoring device on the individual. In one method, the technician locates the continuous-monitoring device on the arm. It is contemplated that the technician may locate the continuous-monitoring device on other locations. The continuous-monitoring device is adapted to process, calibrate, display, store and/or transmit information related to the disease or condition marker.

Process A

A method of using a diffusion-based, continuous-monitoring system to analyze for a state of a disease or condition, the method comprising the acts of:

creating at least one diffusion channel in an area of skin;

maintaining the at least one diffusion channel for a desired duration;

continuously monitoring the level of at least one disease/condition marker for the desired duration via a diffusion-based, continuous-monitoring device; and analyzing the levels of the at least one disease/condition marker at the area of skin to determine if the disease or condition associated with the at least one disease/condition marker is present.

Process B

The method of process A wherein the at least one diffusion channel is a plurality of diffusion channels.

Process C

The method of process A wherein the at least one diffusion channel is created by skin abrasion, microporation, microneedle-diffusion enhancement, pressure members, a lancet, ultrasound energy or laser ablation.

Process D

The method of process A wherein the continuous time period is at least 8 hours.

Process E

The method of process A wherein the continuous time period is at least 24 hours.

Process F

The method of process A wherein the diffusion-based, continuous-monitoring system is an electrochemical-monitoring system.

Process G

The method of process A wherein the diffusion-based, continuous-monitoring system is an optical-monitoring system.

Process H

The method of process A further including storing the level of the at least one disease marker.

Process I

The method of process A further including topographically applying a hydrogel or liquid on the skin to assist in enhancing the diffusion of the at least one disease or condition marker and positioning the diffusion-based, continuous monitoring device in communication with the hydrogel or liquid.

Process J

The method of process I wherein the hydrogel or liquid includes a diagnostic element to assist in analyzing the levels of the at least one disease marker at the area of skin.

Process K

The method of process I wherein positioning the monitoring device includes attaching the monitoring device to the skin.

Process L

The method of process A further including displaying the levels of the at least one disease or condition marker on the continuous-monitoring device.

Process M

A method of using a diffusion-based, continuous-monitoring system to analyze for a state of at least one disease or condition, the method comprising the acts of:

providing a diffusion-based, continuous-monitoring device, the device including a communications interface that is adapted to connect with a receiving module via a communications link;

creating at least one diffusion channel in an area of skin;

maintaining the at least one diffusion channel for a desired duration;

continuously monitoring the level of at least one disease or condition marker for the desired duration via the diffusion-based, continuous-monitoring device; and analyzing the levels of the at least one disease or condition marker at the area of skin to determine if the disease or condition associated with the at least one disease or condition marker is present.

Process N

The method of process M further including transmitting information directed to the levels of the at least one disease or condition marker to the receiving module via the communications link.

Process O

The method of process N further including receiving instructions from the receiving module via the communications link.

Process P

The method of process N wherein the transmitting of information is performed on a wireless system.

Process O

The method of process N wherein the transmitting of information is performed on a wired system.

Process R

The method of process N wherein the transmitting of information occurs at intervals between 5 minutes and 4 hours.

Process S

The method of process M wherein the at least one diffusion channel is a plurality of diffusion channels.

Process T

The method of process M wherein the at least one diffusion channel is created by skin abrasion, microporation, microneedle-diffusion enhancement, pressure members, a lancet, ultrasound energy or laser ablation.

Process U

The method of process M wherein the continuous time period is at least 8 hours.

Process V

The method of process M wherein the continuous time period is at least 24 hours.

Process W

The method of process M wherein the diffusion-based, continuous-monitoring system is an electrochemical-monitoring system.

Process X

The method of process M wherein the diffusion-based, continuous-monitoring system is an optical-monitoring system.

Process Y

The method of process M further including storing the levels the at least one disease or condition marker.

Process Z

The method of process M further including displaying the levels the at least one disease or condition marker.

Process AA

A method of using a diffusion-based, continuous-monitoring system to analyze for a heart attack, the method comprising the acts of:

creating at least one diffusion channel in an area of skin;

maintaining the at least one diffusion channel for a desired duration;

continuously monitoring the level of at least one of troponin, creatine phosphokinase, lactate dehydrogenase, and aspartate transaminase via a diffusion-based, continuous monitoring device; and analyzing the levels of the at least one of troponin, creatine phosphokinase, lactate dehydrogenase, and aspartate transaminase at the area of skin to determine the presence of a heart attack.

Process BB

The method of process AA wherein the troponin is continuously monitored.

Process CC

The method of process AA wherein the creatine phosphokinase is continuously monitored.

Process DD

The method of process AA wherein the lactate dehydrogenase is continuously monitored.

Process EE

The method of process AA wherein the aspartate transaminase is continuously monitored.

Process FF

The method of process AA wherein at least two of troponin, creatine phosphokinase, lactate dehydrogenase, and aspartate transaminase are continuously monitored.

Process GG

A method of using a diffusion-based, continuous-monitoring system to analyze for kidney disease, the method comprising the acts of:

creating at least one diffusion channel in an area of skin;

maintaining the at least one diffusion channel for a desired duration;

continuously monitoring the level of blood urea nitrogen and/or creatinine via a diffusion-based, continuous monitoring device; and analyzing the levels of the blood urea nitrogen and/or creatinine at the area of skin to determine if kidney disease is present.

Process HH

The method of process GG wherein the level of blood urea nitrogen is continuously monitored.

Process II

The method of process GG wherein the level of creatinine is continuously monitored.

Process JJ

The method of process GG wherein at the levels of blood urea nitrogen and creatinine are continuously monitored.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

What is claimed is:

1. A method of using a diffusion-based, continuous-monitoring system to analyze for a state of a disease or condition, the method comprising the acts of:

creating at least one diffusion channel in an area of skin;

applying a hydrogel on the skin, the hydrogel being configured to enhance diffusion from the at least one diffusion channel;

maintaining the at least one diffusion channel for a desired duration;

continuously monitoring the level of at least one disease/condition marker for the desired duration via a diffusion-based, continuous-monitoring device; and analyzing the levels of the at least one disease/condition marker at the area of skin to determine if the disease or condition associated with the at least one disease/condition marker is present.

2. The method of claim 1 wherein the at least one diffusion channel is a plurality of diffusion channels.

3. The method of claim 1 wherein the desired duration is a continuous time period of at least approximately 8 hours.

4. The method of claim 1 wherein the desired duration is a continuous time period of at least approximately 24 hours.

5. The method of claim 1 wherein the diffusion-based, continuous-monitoring system is an electrochemical-monitoring system.

6. The method of claim 1 wherein the diffusion-based, continuous-monitoring system is an optical-monitoring system.

7. The method of claim 1 further including storing the level of the at least one disease marker.

8. The method of claim 1 further including positioning the diffusion-based, continuous-monitoring device in communication with the hydrogel or liquid.

9. The method of claim 1 wherein the continuously monitoring is of the level of blood urea nitrogen and/or creatinine, and the levels of the blood urea nitrogen and/or creatinine at the area of skin is being analyzed to determine if kidney disease is present.

10. The method of claim 9 wherein the level of blood urea nitrogen is continuously monitored.

11. The method of claim 9 wherein the level of creatinine is continuously monitored.

12. The method of claim 9 wherein at least the levels of blood urea nitrogen and creatinine are continuously monitored.

13. A method of using a diffusion-based, continuous-monitoring system to analyze for a state of at least one disease or condition, the method comprising the acts of:

providing a diffusion-based, continuous-monitoring device, the device including a communications interface that is adapted to connect with a receiving module via a communications link;

creating at least one diffusion channel in an area of skin via a channel-creating mechanism, the channel-creating mechanism being separate and distinct from the diffusion-based, continuous-monitoring device;

applying a hydrogel on the skin, the hydrogel being configured to enhance diffusion from the at least one diffusion channel maintaining the at least one diffusion channel for a desired duration;

continuously monitoring the level of at least one disease or condition marker for the desired duration via the diffusion-based, continuous-monitoring device; and analyzing the levels of the at least one disease or condition marker at the area of skin to determine if the disease or condition associated with the at least one disease or condition marker is present.

14. The method of claim 13 further including transmitting information directed to the levels of the at least one disease or condition marker to the receiving module via the communications link.

15. The method of claim 14 further including receiving instructions from the receiving module via the communications link.

16. The method of claim 14 wherein the transmitting of information occurs at intervals between 5 minutes and 4 hours.

17. The method of claim 13 further including storing the levels the at least one disease or condition marker.

* * * * *